United States Patent

Moriya et al.

Patent Number: 5,995,216
Date of Patent: *Nov. 30, 1999

[54] PATTERN INSPECTION APPARATUS

[75] Inventors: Kazuo Moriya; Kazumi Fujimoto, both of Ageo, Japan

[73] Assignee: Mitsui Mining & Smelting Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/794,394

[22] Filed: Feb. 6, 1997

[30] Foreign Application Priority Data

Feb. 16, 1996 [JP] Japan ................................ 8-052538

[51] Int. Cl.$^6$ ............................ G01B 11/02; H04N 7/18
[52] U.S. Cl. ......................... 356/237; 356/394; 348/126
[58] Field of Search ............................. 356/237, 394; 348/126

[56] References Cited

U.S. PATENT DOCUMENTS

| | | | |
|---|---|---|---|
| 5,113,565 | 5/1992 | Cipolla et al. | 29/25.01 |
| 5,452,368 | 9/1995 | LeBeau | 382/145 |
| 5,490,084 | 2/1996 | Okubo et al. | 348/126 |
| 5,617,209 | 4/1997 | Svetkoff et al. | 356/376 |
| 5,648,853 | 7/1997 | Stern et al. | 356/394 |

*Primary Examiner*—Robert H. Kim
*Assistant Examiner*—Zandra V. Smith
*Attorney, Agent, or Firm*—Kubovcik & Kubovcik

[57] ABSTRACT

A pattern inspection apparatus for inspecting an abnormality in a pattern of a plurality of straight lines which are arranged in parallel in a direction perpendicular to the longitudinal direction includes a data acquisition means for acquiring, by photoelectric conversion, first and second image data of the straight lines on first and second lines which pass first and second points at different positions along the straight lines, respectively, and are perpendicular to the straight lines, and a data processing means for detecting the abnormality in the straight lines on the basis of a difference between the first and second image data. The pattern is a pattern of, e.g., inner leads of a TAB tape. When density changes of the first and second image data at a position x along the first and second lines can be approximated by $\sin^2 x$, the data processing means can detect the abnormality by using a relationship established between a phase difference and a density difference between the two changes.

4 Claims, 6 Drawing Sheets

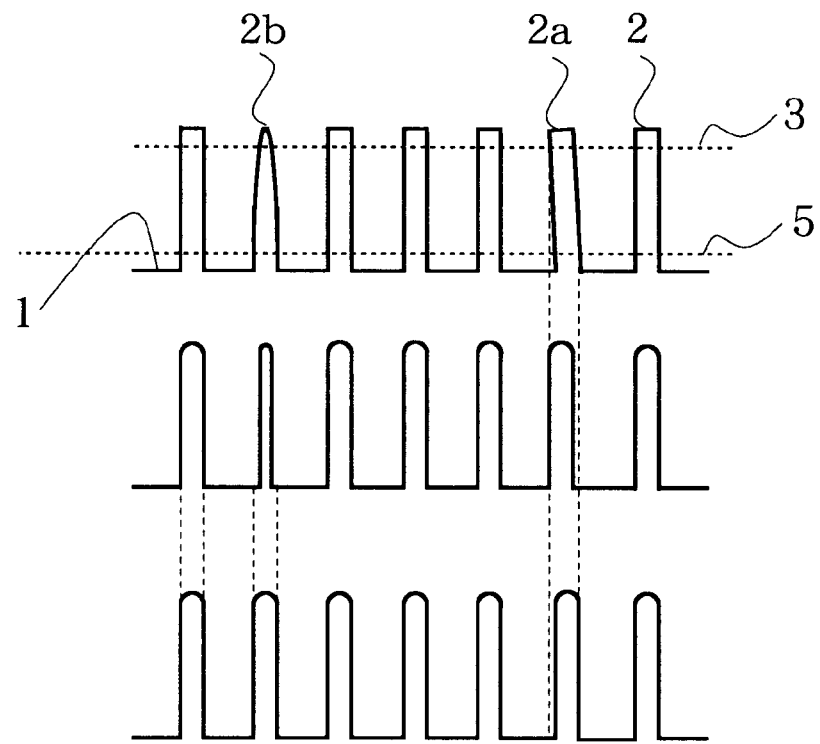
Fig. 2A
Fig. 2B
Fig. 2C
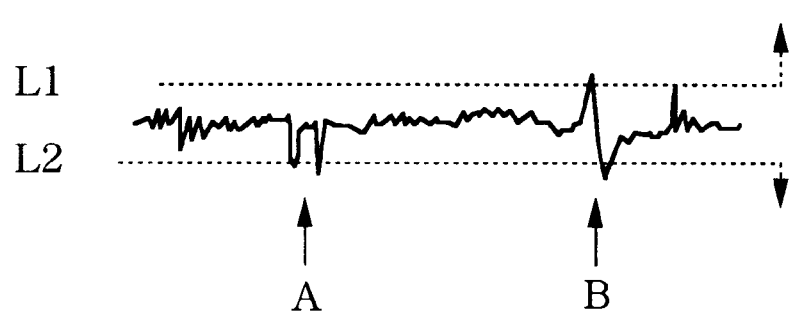
Fig. 2D

PATTERN INSPECTION APPARATUS

BACKGROUND OF THE INVENTION

1. Field of the Invention

The present invention relates to an apparatus for inspecting an abnormality such as a bend in a pattern of a plurality of straight lines such as the inner leads of a TAB tab (tape carrier), which are arranged in parallel in a direction perpendicular to the longitudinal direction.

2. Prior Art

Devices which require inspection of the bend of lead lines thereof include a device in which one end of each lead line 2 is released, as shown in FIG. 6, and a device is which both ends of each lead line 2 are held by a substrate 1, as shown in FIG. 7. Particularly, inner leads for TAB (Tape Automated Bonding) are cantilevered, as shown in FIG. 6, and their distal ends apt to be bent (bowed).

Conventionally, such a bend of lead lines is inspected mainly by visual inspection. In the visual inspection, however, the inspection standard or measurement value varies depending on inspectors, so no quantitative evaluation can be performed. In inspection of the bend of inner leads, detection of a bend of about 10 $\mu$m is required. When the image data of inner leads is to be subjected to binarization for automatic measurement, measurement with a high resolution and a plurality of fields must be performed, resulting in a complex apparatus arrangement and a decrease in processing speed.

SUMMARY OF THE INVENTION

It is an object of the present invention to provide an inspection apparatus for inspecting the bend of a pattern, which can perform high-speed processing with a simple arrangement.

In order to achieve the above object, according to the present invention, there is provided a pattern inspection apparatus for inspecting an abnormality in a pattern of a plurality of straight lines which are arranged in parallel in a direction perpendicular to the longitudinal direction, comprising data acquisition means for acquiring, by photoelectric conversion, first and second image data of the straight lines on first and second lines which pass first and second points at different positions along the straight lines, respectively, and are perpendicular to the straight lines, and data processing means for detecting the abnormality in the straight lines on the basis of a difference between the first and second image data. The pattern is a pattern of, e.g., inner leads of a TAB tape.

When density changes of the first and second image data at a position x along the first and second lines can be approximated by $\sin^2 x$, the data processing means can detect the abnormality by using a relationship established between a phase difference and a density difference between the two changes of the first and second image data.

BRIEF DESCRIPTION OF THE DRAWINGS

FIG. 2A to 2D are views for explaining the operation of the apparatus shown FIG. 1;

DESCRIPTION OF THE PREFERRED EMBODIMENT

Figure 1:
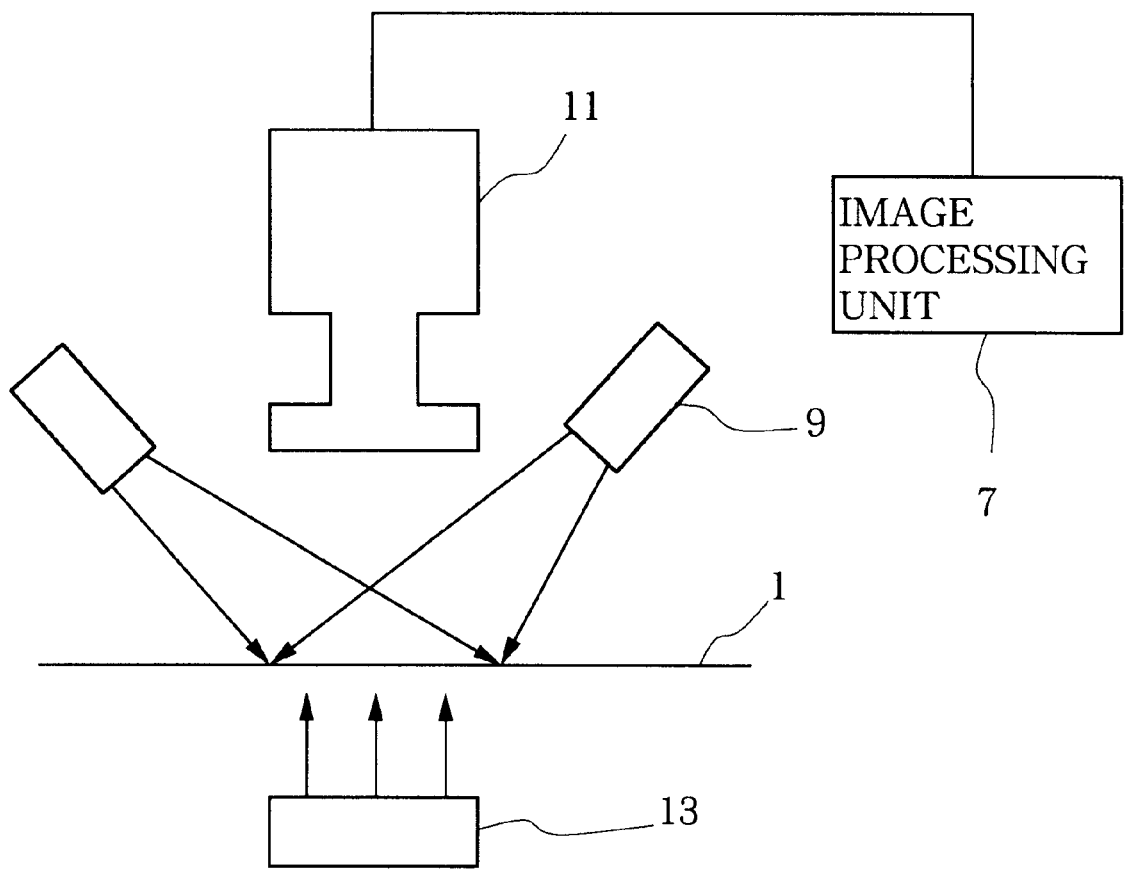
FIG. 1 is a schematic view showing a pattern inspection apparatus according to an embodiment of the present invention.

FIG. 1 is a schematic view showing a pattern inspection apparatus according to an embodiment of the present invention. This inspection apparatus inspects the presence/absence of an abnormality such as a bend (e.g., bow or deformation) of inner leads for TAB. As shown in FIG. 2A, inner leads have a pattern of a plurality of straight line leads 2 on a TAB tape 1, which are arranged in parallel in a direction perpendicular to the longitudinal direction. As shown in FIGS. 1 and 2A, this inspection apparatus comprises a data acquisition means for acquiring, by photoelectric conversion, the first and second image data of the leads 2 on first and second lines 3 and 5 which pass first and second points at different positions along the longitudinal direction of the leads 2, respectively, and are perpendicular to the longitudinal direction of the leads 2, and an image processing unit 7 for determining the presence/absence of an abnormality such as the bend of the leads 2 on the basis of the difference between the first and second image data. The data acquisition means has an illumination means 9 for illuminating the TAB tape 1, and a TV camera 11 for sensing the inner leads on the TAB tape 1 illuminated by the illumination means 9. An illumination means 13 for illuminating the TAB tape 1 from the lower surface side may be used in place of the illumination means 9. Alternatively, the two illumination means may be alternately used to perform inspection using both reflected light and transmitted light.

A plurality of line sensors may be arranged in place of the TV camera 11. Alternatively, one line sensor may be used to perform inspection while moving the TAB tape.

In this arrangement, the image data of the inner leads, which is obtained through TV camera 11, is fetched by the image processing unit 7. The image processing unit 7 obtains intensity profiles along the lines 3 and 5 shown in FIG. 2A, as shown in FIGS. 2B and 2C, and also obtains a difference signal between these data (FIG. 2D). If a lead 2a of the inner leads is bent, the difference signal has a portion B where a high-intensity portion is adjacent to a low-intensity portion in correspondence with the lead 2a portion, as shown in FIG. 2D. If a tapered lead 2b is present, the difference signal has low-intensity portions corresponding to the both side portions of the lead 2b. The image processing unit 7 can check whether the difference signal has a portion with a predetermined intensity L1 or more, or a portion with a predetermined intensity L2 or less, thereby detecting the presence of an abnormality such as the bend or taper of leads.

Figure 3:
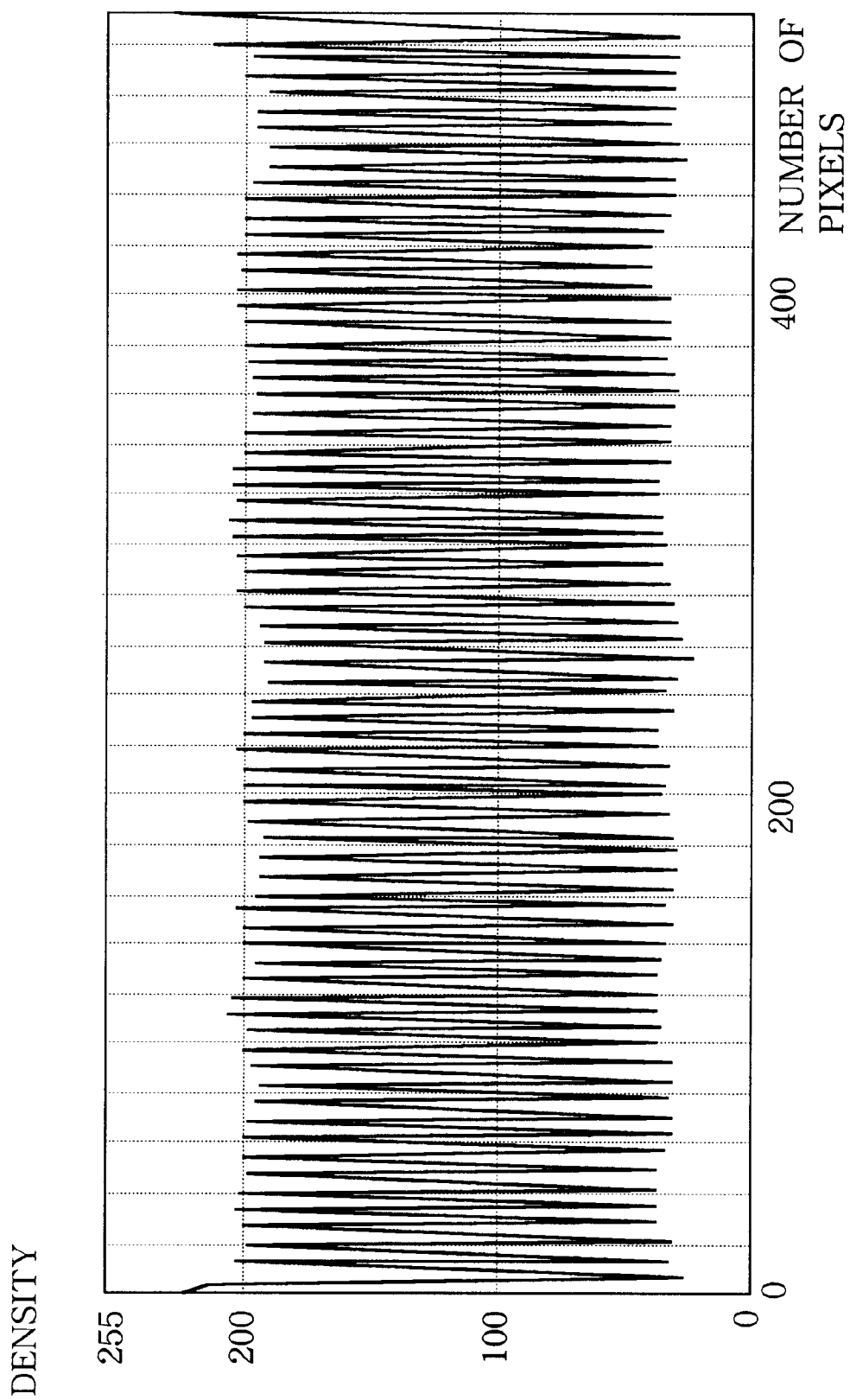
FIG. 3 is a graph showing density data processed by the apparatus shown in FIG. 1.
Figure 4:
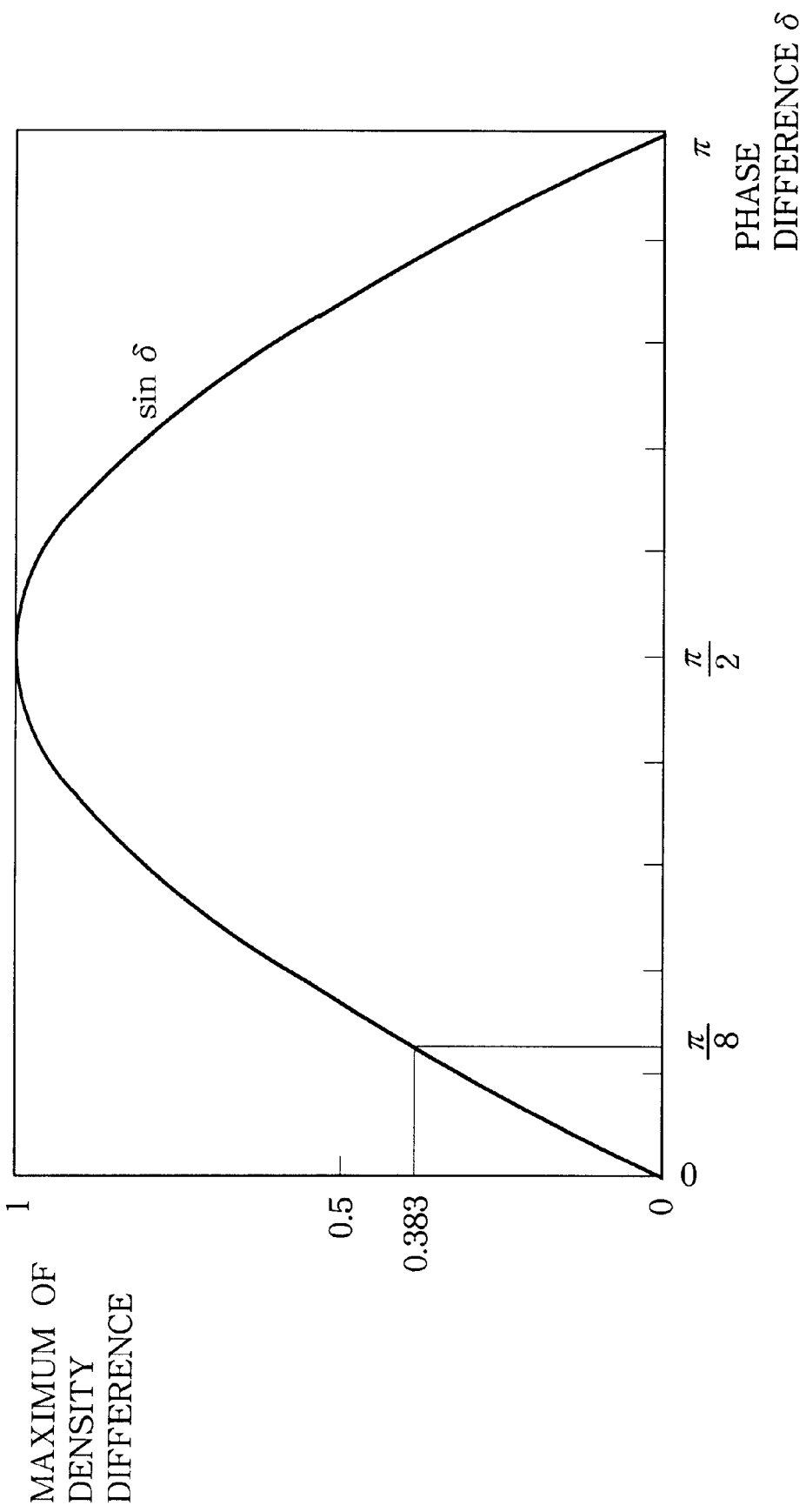
FIG. 4 is a graph showing a variation in maximum value of a density difference in accordance with a phase difference.
Figure 5:
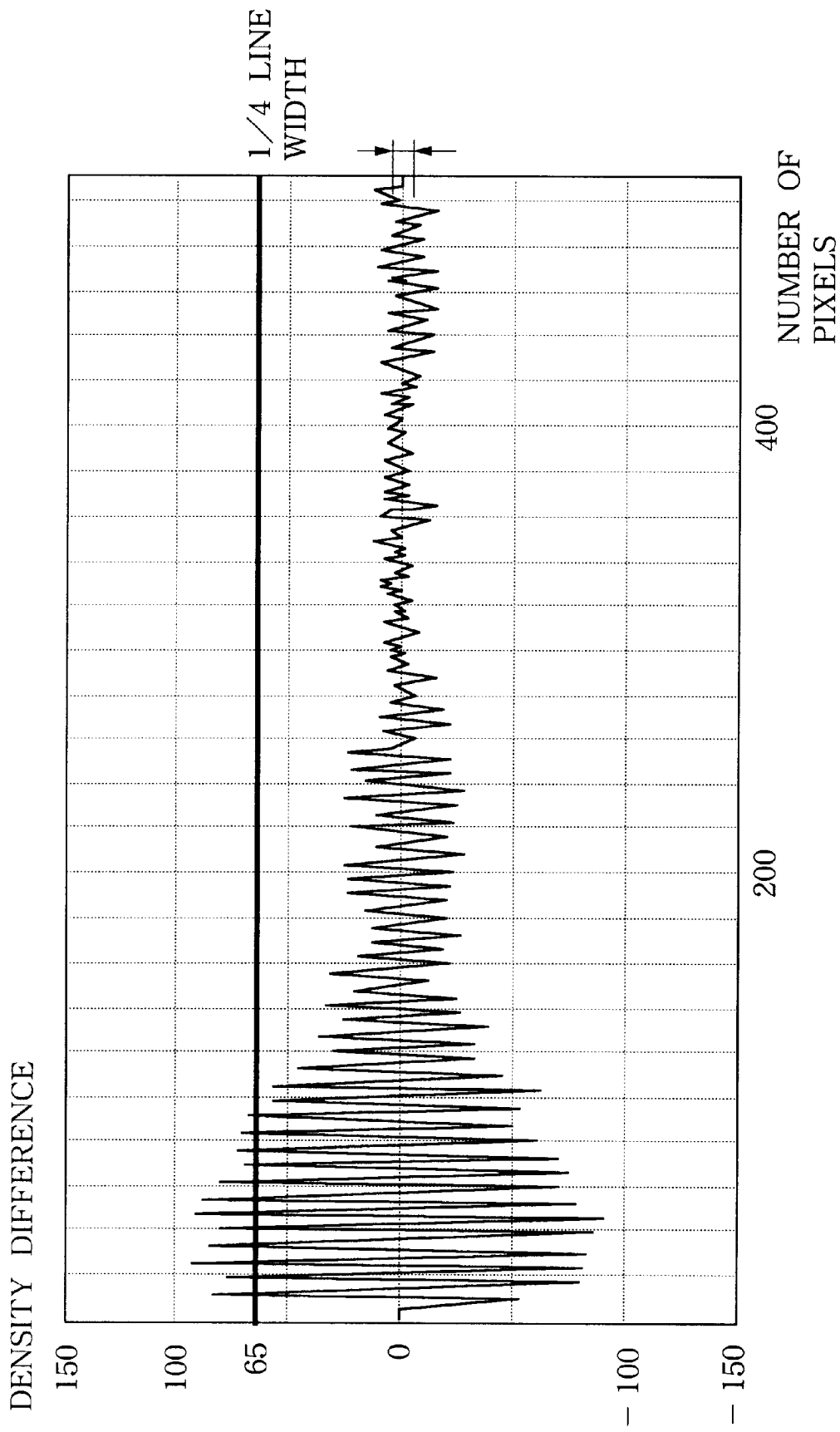
FIG. 5 is a graph showing a density difference observed when a bend is actually inspected by the apparatus shown in FIG. 1.
Figure 6:
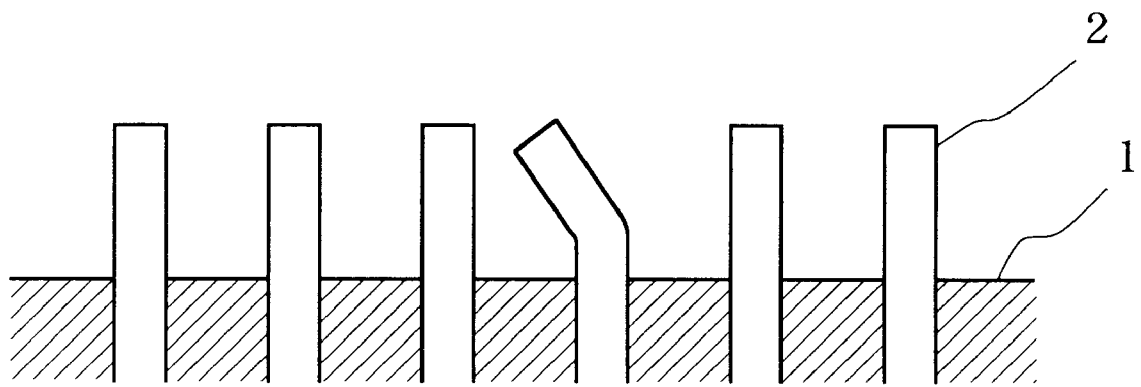
FIG. 6 is a view showing lead lines each of which has one end released.
Figure 7:
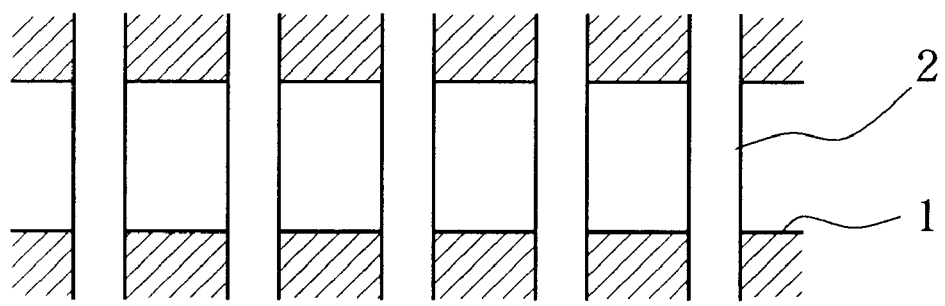
FIG. 7 is a view showing lead lines each of which has both ends held by a substrate.

A case in which density changes at a position x of the image data along the lines 3 and 5 can be approximated by $\sin^2 x$ will be described below. The pitch of the leads 2 is 90 $\mu$m, the number of pixels of image data corresponding to this pitch is 7, the line width of the lead 2 is 45 $\mu$m, and the number of pixels corresponding to this line width is 3.5. FIG. 3 shows a density change along the line 3 or 5. When the density changes along the lines 3 and 5 are approximated by $\sin^2 x$, the density difference between the changes is represented by $\sin^2 x - \sin^2(x-\delta) = \sin^2 x - \cos^2(x-\delta+\pi/2) = -\cos$ $(2x-\delta+\pi/2)\times\cos(\delta-\pi/2)=-\cos(2x-\delta+\pi/2)\times\sin\delta$, where $\delta$ is the phase difference between the density changes. As is apparent, the maximum value of the density difference varies in accordance with the phase difference $\delta$. FIG. 4 shows this relationship. The image processing unit 7 determines the presence/absence of an abnormality such as the bend of the lead 2 by using the relationship established between the phase difference $\delta$ and the density difference.

When the lead 2 is bent by ¼ the width, the phase shifts by $\pi/8$. Assume that a bend corresponding to at least ¼ the width is determined as an abnormality. When the density difference equals or exceeds the maximum value of the density difference when the phase difference $\delta$ is $\pi/8$, i.e., $\sin(\pi/8)=0.383$, an abnormality may be determined.

The density changes are approximated by $\sin^2 x$. In fact, assuming that the density of pixel data on the lead 2 is 200, and the background density is 30, the maximum value of the density difference when the phase difference $\delta$ is $\pi/8$ is $(200-30)\times\sin(\pi/8)=65.06$, and this value is set as a threshold value. If, in the density difference between the respective pixels of the image data along the lines 3 and 5 has a portion with a value larger than the threshold value, it can be determined that the lead line at this portion is bent, between the lines 3 and 5, by at least ¼ width of the lead line.

In this manner, the density changes along the lines 3 and 5 are approximated by $\sin^2 x$, and a bend is detected using the relationship established between the phase difference and the difference between the changes. With the processing, the bend of inner leads for TAB can be inspected with a wide field (10 to 15 mm square) based on a low resolving power (15 to 20 $\mu$m/pixel), i.e., with a simple arrangement at a high speed.

In this embodiment, only two lines, i.e., the lines 3 and 5 are used as the first and second lines. However, when more lines are used, and the densities between these lines are compared, the degree of bend can be inspected in more detail.

As has been described above, according to the present invention, the bend of a straight line pattern is detected on the basis of the difference between image data on the first and second lines. Therefore, inspection can be performed at a high speed without performing image processing such as binarization with a large processing amount.

The density changes of the image data along the first and second lines are approximated by $\sin^2 x$, and a bend is detected using the relationship established between the phase difference $\delta$ and the density difference between these changes. With the processing, inspection can be performed with a wide field based on a low resolution, i.e., with a simple arrangement at a higher speed.

What is claimed is:

1. A pattern inspection apparatus for inspecting an abnormality in a pattern of a plurality of straight lines which are arranged in parallel in a direction perpendicular to said straight lines, comprising:

data acquisition means for acquiring, by photoelectric conversion, image data consisting of density changes of first and second image data of said straight lines at first and second points spaced apart along the length of said straight lines and corresponding to the intersection of said straight lines with first and second lines that are parallel to each other and are perpendicular to said straight lines; and data processing means for detecting the abnormality in said straight lines on the basis of a difference between density changes of the first and second image data by checking whether the difference signal has portion with a predetermined intensity L1 or more, or a portion with a predetermined intensity L2 or less.

2. An apparatus according to claim 1, wherein said pattern is a pattern of inner leads of a TAB tape.

3. A pattern inspection apparatus for inspecting an abnormality in a pattern of a plurality of straight lines which are arranged in parallel in a direction perpendicular to said straight lines, comprising:

data acquisition means for acquiring, by photoelectric conversion, first and second image data of said straight lines on first and second lines which pass first and second points at different positions along said straight lines, respectively, and are perpendicular to said straight lines; and data processing means for detecting the abnormality in said straight lines on the basis of a difference between the first and second image data, wherein density changes of the first and second image data at a position x along the first and second lines can be approximated by $\sin^2 x$, and said data processing means detects the abnormality by using a relationship established between a phase difference and a density difference between the two changes.

4. An apparatus according to claim 3, wherein the density difference between the changes is represented by $\sin^2 x - \sin^2(x-\delta)$ where $\delta$ is the phase difference between the density changes.

* * * * *